United States Patent [19]

Lale et al.

[11] Patent Number: 4,609,870

[45] Date of Patent: Sep. 2, 1986

[54] LIFT OFF COMPENSATION OF EDDY CURRENT CRACK DETECTION SYSTEM BY CONTROLLING DAMPING RESISTANCE OF OSCILLATOR

[75] Inventors: Peter G. Lale, Harpenden; Donald H. Hocking, St. Albans, both of United Kingdom

[73] Assignee: Hocking Electronics Limited, Hertsfordshire, England

[21] Appl. No.: 650,667

[22] Filed: Sep. 13, 1984

Related U.S. Application Data

[63] Continuation-in-part of Ser. No. 358,575, Mar. 16, 1982, abandoned.

[30] Foreign Application Priority Data

Mar. 27, 1981 [GB] United Kingdom ............... 8109704

[51] Int. Cl.4 ............... G01N 27/72; G01N 27/82; G01R 33/12
[52] U.S. Cl. ............... 324/225; 324/237; 331/65; 331/109
[58] Field of Search ............... 324/225, 234, 236–243; 331/109, 182, 183, 184, 65

[56] References Cited

U.S. PATENT DOCUMENTS

| | | | |
|---|---|---|---|
| 3,396,193 | 2/1968 | Nordahl | 331/109 |
| 4,274,054 | 6/1981 | Savidge et al. | 324/225 |
| 4,387,338 | 6/1983 | Hecht et al. | 324/236 |

Primary Examiner—Ernest F. Karlsen
Assistant Examiner—Walter E. Snow
Attorney, Agent, or Firm—Hayes, Davis & Soloway

[57] ABSTRACT

An eddy current crack detection system has an inductive probe coil forming part of an oscillatory circuit. The coil voltage is fed to a measuring device a change in amplitude of the coil voltage being used as an indication of a crack. In order to compensate for lift-off in the amplitude of the coil voltage, a control signal is generated related to the magnitude of lift-off, and controls the value of a variable damping resistor in the oscillatory circuit.

9 Claims, 7 Drawing Figures

LIFT OFF COMPENSATION OF EDDY CURRENT CRACK DETECTION SYSTEM BY CONTROLLING DAMPING RESISTANCE OF OSCILLATOR

This is a continuation-in-part; of application Ser. No. 358,575 filed Mar. 16, 1982, now abandoned.

The present invention relates to eddy current crack detection systems.

Eddy current systems are in common use for the detection of cracks in metals. In one form a probe coil is driven with alternating current and placed on the surface of the metal to be investigated. Eddy currents are induced in the metal which in turn react on the probe coil, affecting its impedance. A crack in the metal surface will alter the magnitude and distribution of eddy currents, thereby altering the impedance of the probe coil. This change in impedance is used to detect the crack and to estimate its magnitude.

The coil impedance will however also be altered if the probe is lifted off the metal surface. Even very small degress of lift-off such as 0.1 mm can cause impedance changes which may be considerably larger than those produced by the small cracks which are required to be detected.

Lift-off variation may occur through surface roughness, paint thickness variations, or changes in probe angle. Where for example inspection for cracks is required during in-service checks on aircraft wings, the metal surface will be painted with a thickness of paint that will vary and cause significant variation in probe coil impedance.

In U.S. Pat. No. 4,387,338 (Hecht et al) an eddy current testing system is disclosed incorporating a method of compensating for lift-off using two resonant circuits adjusted to neighbouring frequencies. The probe coil impedance forms a part of the inductive components of one of the resonant circuits. The frequency of the other of the resonant circuits is preset at an optimum value which is dependent upon the conductivity of the metal body to be tested. Compensation for varying amounts of lift off depends upon the resultant changes in amplitude and frequency in said one resonant circuit brought about by lift-off substantially balancing out in their effect on the output voltage of the said other resonant circuit whose frequency has been preset and hence produce a reduced variation in voltage output signal to the measuring instrument of the testing system.

The presetting of the frequency of said other resonant circuit involves a setting-up procedure which comprises comparing a series of voltage values with the probe coil lifted off the metal body to be tested, with a series of voltage values with the probe coil in contact with the metal body to be tested. A control arrangement produces from this comparison a control voltage which controls the bias of varacter diodes used to provide capacitance in the said other of the resonant circuits. Thus the capacitance and hence the frequency of the said other resonant circuit is pre-set in dependence upon the value of the control voltage. Thereafter during the testing procedure the frequency remains at the preset value, governed by the preset value of the varacter diode bias. No control signal is used for dynamic adjustment during crack detection. Further the preset value of frequency has been determined solely from the two extreme probe positions and therefore may not be accurate for all positions intermediate these extremes.

The principal object of the present invention is to provide a method of dynamic compensation for lift-off such that the amount of compensation varies in dependence upon the degree of list-off as the crack detection procedure is being carried out.

A further object of the present invention is to provide a dynamic control to compensate accurately for lift-off so that the measured changes in output of the detection system due to small cracks are not masked by lift-off.

According to one aspect of the present invention there is provided a method of eddy current crack detection using an inductive probe coil forming part of an oscillatory circuit, the amplitude of the oscillatory voltage across the probe coil being monitored by a measuring device whereby to detect cracks, characterised in that in order to substantially nullify the effect of lift-off on the amplitude of the oscillator voltage a control signal is produced related to the instantaneous magnitude of lift-off and said control signal continuously controls the value of damping resistance in said oscillatory circuit so that the amplitude of the oscillatory voltage does not vary substantially with lift-off.

In one form of the invention the probe coil may form part of an oscillatory circuit, whose frequency is governed by the probe inductance. Changes in lift-off cause changes in the probe inductance and therefore cause changes in the frequency and period of the current in the probe coil. This period or frequency variation may be used to produce the control signal.

In another form of the invention, the coil is driven at a fixed frequency and the change in phase with lift-off is used to generate the control signal.

As lift-off occurs, probe coil damping by the metal is reduced, and the amplitude of oscillation tends to increase. The control signal is used to increase coil damping by increasing the effective damping resistance as lift-off occurs, in order to maintain constant coil amplitude or constant output to a meter measuring coil amplitude.

Cracks will still show up, since although they cause the probe inductance to change (with non-magnetic metals) in the same direction as for lift-off, probe damping changes in the opposite direction. A probe circuit which is compensated for lift-off by increasing the effective damping resistance as lift-off occurs, in order to maintain constant probe coil amplitude, will therefore show a reduction in amplitude in the presence of cracks in non-magnetic materials.

Cracks in magnetic materials may also in similar manner be made to show up, when compensation for lift-off is applied.

According to another aspect of the invention there is provided an eddy current crack detection system comprising an inductive probe coil forming part of an oscillatory circuit and a measuring device arranged to monitor the amplitude of the oscillatory voltage across the probe coil whereby to detect cracks, characterised in that in order to substantially nullify the effect of lift-off on the amplitude of the oscillatory voltage a variable electrical resistance is provided in the oscillatory circuit and control means responsive to the instantaneous magnitude of lift-off provide a control signal for continuously varying the value of said resistance and hence the value of the damping resistance in the oscillatory circuit so that the amplitude of the oscillatory voltage does not vary substantially with lift-off.

The variation of damping resistance that is needed with change in phase or period or frequency is in general not a strictly linear function. The electrical resistance (for non-magnetic metals) therefore requires to be increased more rapidly by the control signal as lift off commences than when the probe is further from the metal.

The invention will now be further described by way of example with reference to the accompanying drawings in which.

Figure 1:
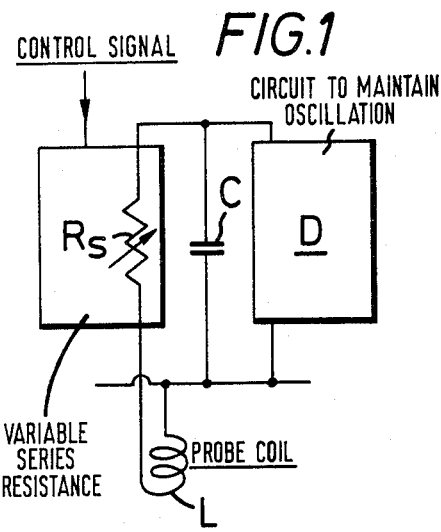
FIG. 1 illustrates the probe coil as part of an oscillatory circuit with a variable series resistance to control damping.
Figure 2:
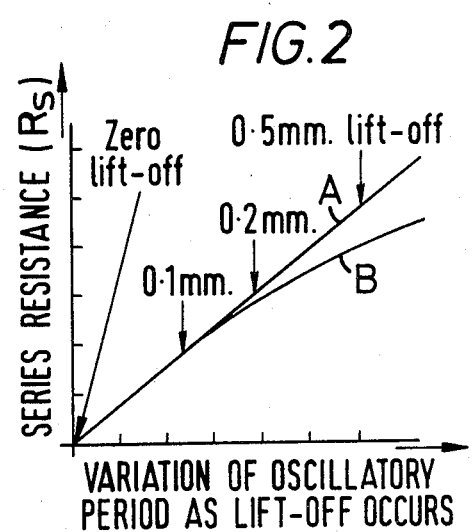
FIG. 2 illustrates a linear relationship A between series damping resistance and change in oscillatory period and a non-linear relationship by curve B.

Referring to FIGS. 1 and 2, probe coil L is connected in a tuned circuit with capacitor C and a series connected damping resistance $R_s$. Driving circuit D is provided to maintain oscillation of the tuned circuit. The voltage output from the coil is fed to a meter. In use the probe is moved relatively to the surface of a metal body being investigated and a change in probe output voltage is used as an indication of a crack.

As previously discussed one of the problems is to maintain constant the amplitude of the oscillatory voltage across the probe coil and hence constant output to the meter when lift-off occurs. In accordance with the invention this is achieved by continuously varying the damping resistance $R_s$ by a control signal related to the frequency or period or phase of the output signal, which itself is a function of the instantaneous magnitude of lift-off.

Line A of FIG. 2 shows a linear relationship between series damping resistance $R_s$ and variation of oscillatory period and which will maintain an acceptably constant output amplitude from the probe coil with lift-off.

Curve B of FIG. 2 is typical of the variation of effective series damping resistance that is required for non-magnetic metals to give accurate compensation for lift-off variation up to say 0.5 mm.

Figure 3:
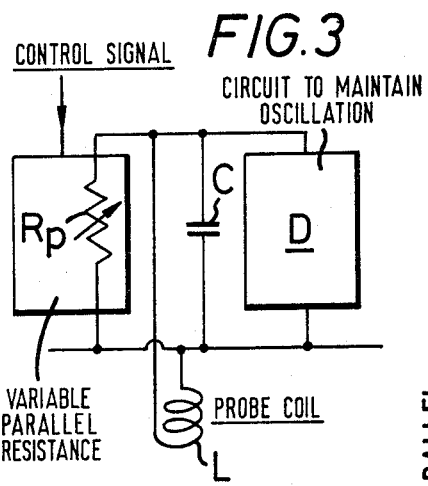
FIG. 3 illustrates a circuit for controlling damping by means of a parallel resistance.
Figure 4:
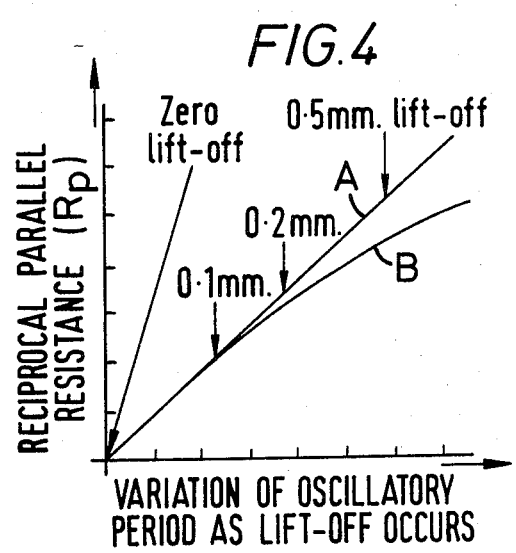
FIG. 4 shows a plot of the reciprocal of damping resistance against change in oscillatory period, line A representing a linear relationship and curve B a non-linear relationship.

Instead of using series damping resistance $R_s$, parallel damping resistance $R_p$ as shown in FIG. 3 can be used. FIG. 4 shows line A and curve B corresponding to FIG. 2, but the relationship is of course between variation of oscillatory period and the reciprocal of the parallel resistance.

Figure 5:
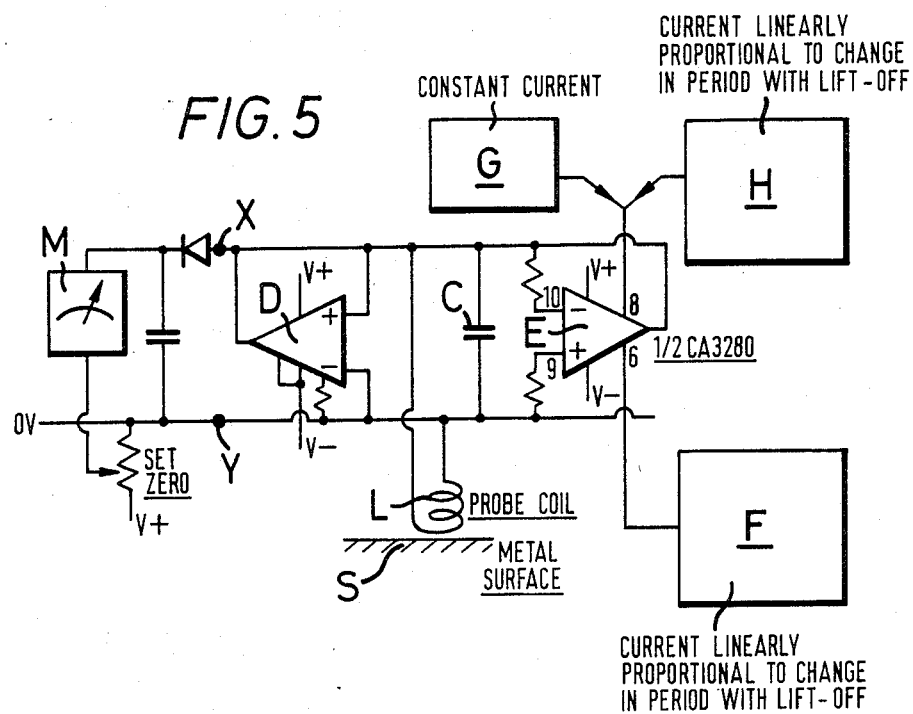
FIG. 5 illustrates one circuit for non-magnetic metals and which corresponds in principle to the circuit of FIG. 3.

FIG. 5 illustrates one circuit for non-nagnetic metals utilising parallel damping resistance that may be used to compensate for lift-off so that a constant probe coil voltage is maintained. Transconductance amplifier D provides +ve current feedback to the oscillatory circuit of the probe coil L and parallel capacitor C to maintain an oscillatory current in the probe coil L. The probe in use is positioned close to the metal surface S. Transconductance amplifier E is arranged to provide an antiphase current which is proportional to the probe voltage. The amplifier E therefore acts as a parallel damping resistance, whose value depends on the amplifier gain. The gain is proportional to the current flowing into pin 6 of amplifier E. This current is controlled by a generator F which is arranged to give a current close to zero when lift-off is zero, and increase linearly with the increasing period of oscillation as the probe is lifted off. When suitably scaled this provides compensation for lift-off effectively following the line A of FIG. 4.

Increasing the current at the 'diode' terminal pin 8 of amplifier E causes a reduction in amplifier gain and reduces the damping, i.e. reduces the slope of line A in FIG. 4. Two currents are fed into this terminal. One is constant and is fed from generator G and provides the initial slope along line A of FIG. 4. The second current is provided by current generator H and is arranged to be zero when lift-off is zero, and to increase linearly with the increasing period of oscillation as lift-off occurs. This results in reducing the gain of amplifier E progressively with lift-off and damping can be adjusted to follow curve B of FIG. 4 so that accurate compensation for lift-off is provided and the reading of meter M remains almost constant with lift-off.

Figure 7:
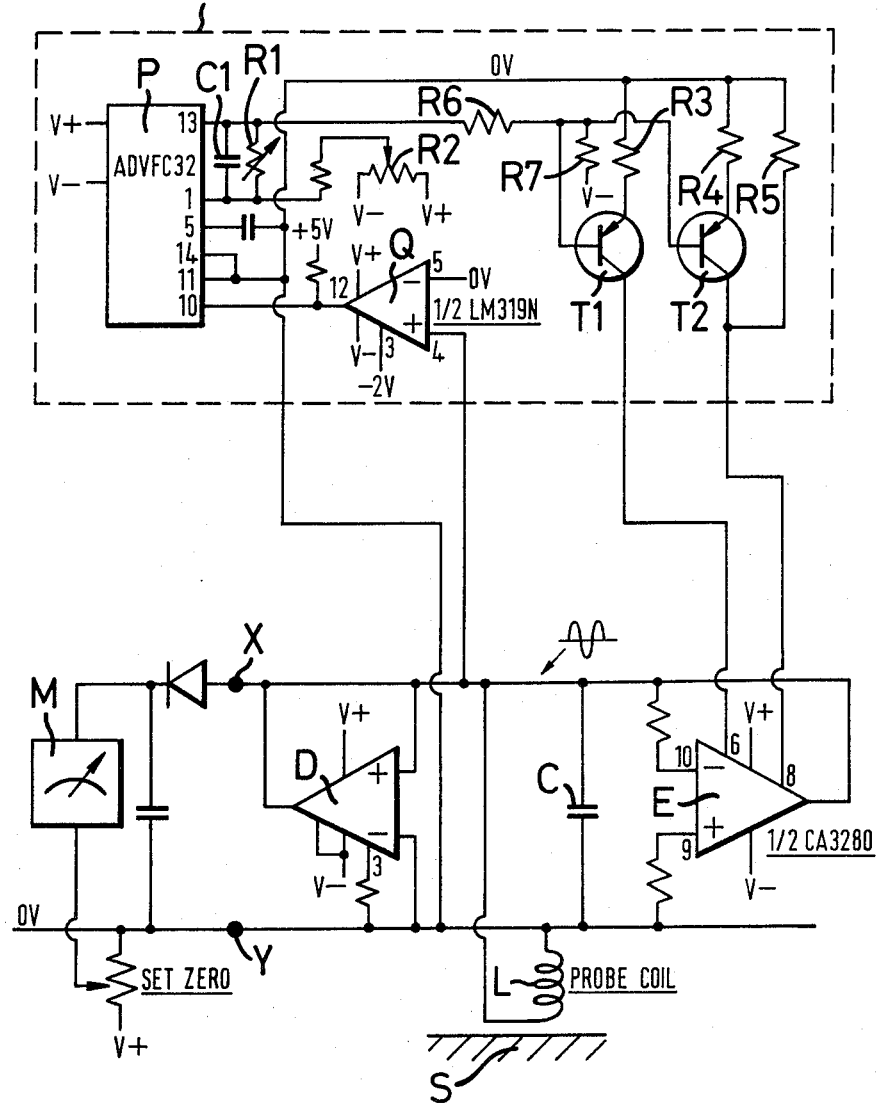

FIG. 7 shows the circuit elements of FIG. 5 together with the schematic boxes F G H redrawn as actual circuits within outline W in FIG. 7.

Comparator Q switches at each zero crossing of the probe coil voltage to provide a square wave input at terminal 10 of P. Integrated circuit P is a frequency-to-voltage or voltage-to-frequency convertor, connected in its frequency-to-voltage mode. Integrated circuit P may, for example, comprise an ADVF C32 manufactured by Analogue Devices, Inc. C1 sets the integrating time constant and R1 sets the gain of the output amplifier within P, controlling the magnitude of the output voltage change at pin 13 for a given change in frequency. The change in output voltage is proportional to the change in frequency of the probe coil voltage. For small frequency changes the change in output voltage is also approximately proportional to the change in period of the probe coil voltage.

The voltage at 13 of P is DC shifted by R6 and R7, and then controls the current flow in T1 and T2. These currents can be set close to zero at the frequency of the probe coil voltage when the probe is on the metal, by adjustment of R2. The current in T2 is arranged to be small compared to the current in T1. As the probe lifts off the metal the current from T1 into terminal 6 of transconductive amplifier E increases, causing the current gain of E to increase. The current flowing into the output terminal of E is proprotional to the voltage across C (i.e. across resonant circuit LC). The ratio of the voltage across LC to the current into the output terminal of E represents an effective resistance in parallel with LC. This effective resistance is controlled by the current gain of E and hence by the current flowing into terminal 6 of E. Thus changes in the period of the probe coil voltage are arranged by means of Q, P, T1, E to vary the effective resistance in parallel with LC.

The circuit in outline W of FIG. 7 including Q, P, T1 corresponds to the box F of FIG. 5.

The current into pin 8 of E is defined principally by R5, but with some small variation with change in period of the coil voltage by means of T2. A small increase in the current into pin 8 causes a small reduction in the output current flow of E. The circuit in outline W of FIG. 7 including Q, P, T2, corresponds to box H of FIG. 5. Resistor R5 of FIG. 7 corresponds to box G of FIG. 5.

The current into terminal 6 of E in FIG. 7 increases with oscillatory period. Doubling this current halves the effective resistance in parallel with LC. The reciprocal of the parallel resistance is thus made to vary in proportion to the change in oscillatory period. Since oscillatory period varies with lift off, then by setting R1 and R2 appropriately this change in reciprocal parallel resistance can be made to compensate for the fall in coil damping that occurs as the probe is lifted off the metal, i.e. can be made to follow line A of FIG. 4 in order to provide appropriate compensation for lift off.

The current into terminal 8 of E in FIG. 7 varies slightly with oscillatory period and can be set for a range of metals by selection of R4 of FIG. 7 so that curve B of FIG. 4 is followed, giving a more accurate compensation as lift off occurs.

Typically in FIG. 7 the current into terminal 3 of D is set to 1 mA and the meter set-zero control is set so that the meter deflects to half scale with the probe on sound metal. Typically the current into terminal 6 of E is set to 0.1 mA and the current into terminal 6 of E is allowed to vary typically within the range 0 to 0.5 mA.

This system may be compared with other methods of providing lift off compensation, for example, U.S. Pat. No. 4,387,338 (Hecht et al) discussed above. In the system of the present invention described above the effective damping resistance is under continuous dynamic control and any instantaneous change in period or frequency of the oscillating voltage produces a compensating change in damping resistance so that there is no change in amplitude of the oscillating voltage with lift-off as the probe is used to search for defects.

Figure 6:
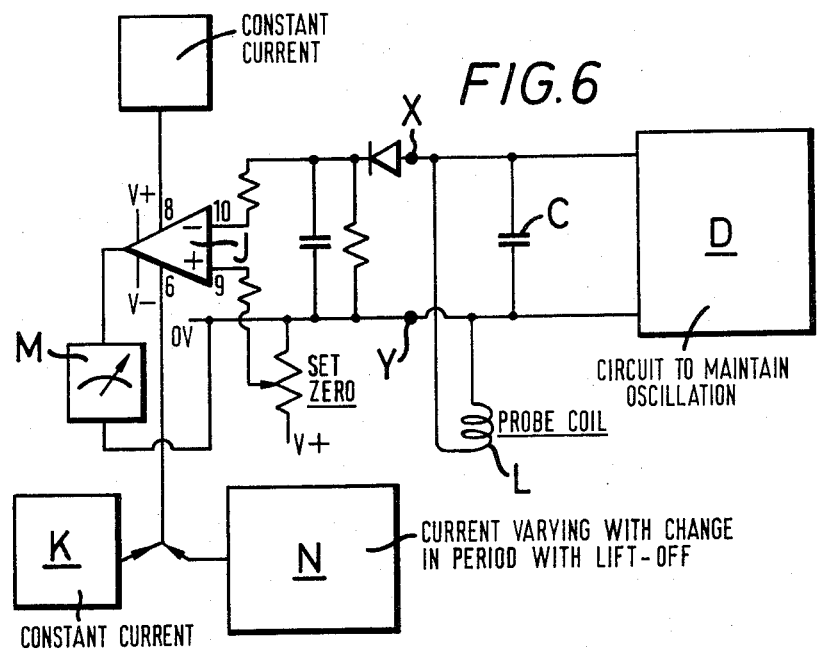
FIG. 6 illustrates a circuit which enables the deflection of a meter connected to a probe to maintain a constant reading of a crack even when the probe is moved away from the metal surface, and FIG. 7 corresponds to FIG. 5 with schematic boxes F, G, H replaced by working circuits.

The meter deflection for a given size of crack will be reduced when the probe is further from the metal surface. An approximate means of compensation for this can be arranged over a limited range of lift-off. FIG. 6 illustrates one circuit that may be used to achieve this compensation. A variable gain transconductance amplifier J is connected between the rectified output voltage from the probe coil L and the indicating member M.

Two currents are fed into terminal 6. One is a constant current fed from generator K to provide the standard gain when lift-off is zero. The second is provided by current generator N which increases as the period of oscillation increases, causing an increase in gain. This second current may be adjusted to compensate approximately for the reduced sensitivity to cracks of the probe coil as lift-off increases.

In the context of the present invention the circuit of FIG. 6 is used with the circuit of FIG. 5 by replacing the circuit to the right of points X,Y in FIG. 6 with the circuit to the right of points X,Y in FIG. 5.

With certain magnetic metals for example mild steel, the probe coil inductance shows an overall increase as the probe approaches the metal surface. Lift-off from the surface in this instance causes a reduction in the period of oscillation. This reduction in period may be used to develop a control signal for increasing the damping with lift-off in a similar manner to that described for non-magnetic materials. A circuit similar to that of FIG. 5 may be used. Further, current fed into pin 8 of amplifier E may be arranged to decrease as lift-off occurs, if this is required for accurate lift-off compensation.

The foregoing method of compensation may also be applied to probes of different configuration than surface probes. Probes designed to rotate within bolt holes for example, may be compensated by similar means. Further, probe coils surrounding metal rods may be compensated by similar means for changes in the rod dimensions, i.e. for changing fill factor.

We claim:

1. An eddy current crack detection system comprising an inductive probe coil forming part of an oscillatory circuit and a measuring device arranged to monitor the amplitude of the oscillating voltage across the probe coil whereby to detect cracks, characterised in that in order to substantially nullify the effect of lift-off on the amplitude of said voltage there is provided a variable electrical resistance in the oscillatory circuit and control means responsive to the instantaneous magnitude of lift-off to provide a control signal for continuously varying the value of said resistance and hence the amount of damping in the oscillatory circuit so that the ampliltude of said voltage does not vary substantially with lift-off.

2. An eddy current crack detection system according to claim 1 wherein said control means is responsive to the change in frequency of said voltage with lift-off.

3. An eddy current crack detection system according to claim 1, wherein a transconductance amplifier is connected in parallel with the probe coil in order to provide the varying electrical resistance in said oscillatory circuit.

4. An eddy current crack detection system according to claim 1, wherein in order to maintain an input voltage to said measuring device substantially constant for a given size of crack, a variable gain amplifier is connected between the output of said probe coil and said measuring device and the gain of said amplifier is varied by a control signal related to the magnitude of lift-off.

5. An eddy current crack detection system according to claim 1, wherein said control means is responsive to the change in phase of said voltage with lift-off.

6. In a method for eddy current crack detection in metal structures comprising the steps of:
   (a) placing an inductive probe coil onto a surface of said structure;
   (b) producing an oscillating voltage across said coil;
   (c) moving said coil over said surface; and
   (d) monitoring the oscillating voltage across said coil thereby to detect cracks in said structure;
the improvement comprising the steps of:
   (e) producing a dynamic control signal continuously responsive to electrical effects in said circuit of changes in the magnitude of lift-off of said coil from said surface;
   (f) controlling damping resistance of said coil responsive to said signal to maintain the amplitude of said voltage substantially constant with changes in magnitude of lift-off, thereby to nullify the effect of lift-off on the amplitude of said voltage.

7. In a method according to claim 6, the further improvement comprising the step of said control signal being responsive to effects on changes in frequency of the current in said coil with changes in said magnitude.

8. In a method according to claim 6, the further improvement comprising the step of said control signal being responsive to effects on changes in phase of said voltage with changes in said magnitude.

9. In a method for eddy current crack detection in metal structures comprising the steps of:

(a) placing an inductive probe coil, which is part of an oscillatory circuit, onto a surface of said structure;
(b) operating said circuit to produce an oscillating voltage across said coil;
(c) moving said coil over said surface; and
(d) monitoring the oscillating voltage across said coil thereby to detect cracks in said structure;
the improvement comprising the steps of:
(e) producing a dynamic control signal continuously responsive to electrical effects in said circuit of changes in the magnitude of lift-off of said coil from said surface;
(f) controlling damping resistance in said circuit responsive to said signal to maintain the amplitude of said voltage substantially constant with changes in magnitude of lift-off, thereby to nullify the effect of lift-off on the amplitude of said voltage.

* * * * *